United States Patent [19]

Condon et al.

[11] 4,206,137
[45] Jun. 3, 1980

[54] THIOALKANOYLALKANOIC ACID COMPOUNDS

[75] Inventors: Michael E. Condon, Lawrenceville; Miguel A. Ondetti, Princeton, both of N.J.

[73] Assignee: E. R. Squibb & Sons, Inc., Princeton, N.J.

[21] Appl. No.: 962,429

[22] Filed: Nov. 20, 1978

Related U.S. Application Data

[63] Continuation-in-part of Ser. No. 890,446, Mar. 27, 1978, abandoned.

[51] Int. Cl.$^2$ ................. C07C 153/09; C07C 61/08
[52] U.S. Cl. ......................... 260/455 R; 560/152; 560/122; 560/123; 560/125; 560/126; 562/507; 562/504; 562/505
[58] Field of Search ............... 260/455 R; 560/152, 560/122, 123, 125, 126; 562/507, 504, 505

[56] References Cited

U.S. PATENT DOCUMENTS

| | | | |
|---|---|---|---|
| 3,098,078 | 7/1963 | Druey et al. | 260/455 R |
| 4,046,889 | 9/1977 | Ondetti | 424/244 |
| 4,053,651 | 10/1977 | Ondetti | 424/319 |

FOREIGN PATENT DOCUMENTS

762575  11/1956  United Kingdom ............ 260/455 R

*Primary Examiner*—Alan L. Rotman
*Assistant Examiner*—Robert C. Whittenbaugh
*Attorney, Agent, or Firm*—Lawrence S. Levinson; Merle J. Smith; Stephen B. Davis

[57] ABSTRACT

Thioalkanoylalkanoic acid compounds and salts thereof having the formula

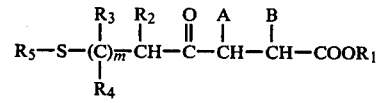

wherein
$R_1$, $R_2$, $R_3$ and $R_4$ each is hydrogen or lower alkyl;
$R_5$ is hydrogen, lower alkanoyl, benzoyl or

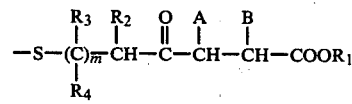

A and B each is hydrogen or join together as a polymethylene chain —$(CH_2)_n$— to complete a 4-, 5- or 6- membered cycloalkyl group, and m is 0 or 1, are angiotensin converting enzyme inhibitors and are useful as hypotensive agents.

25 Claims, No Drawings

THIOALKANOYLALKANOIC ACID COMPOUNDS

This application is a continuation-in-part of application Ser. No. 890,446, filed Mar. 27, 1978, now abandoned.

SUMMARY OF THE INVENTION

This invention relates to new thioalkanoylalkanoic acid compounds which have the formula

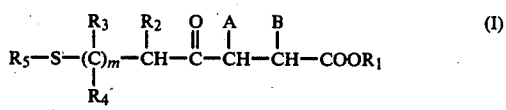

wherein
$R_1$, $R_2$, $R_3$ and $R_4$ each is hydrogen or lower alkyl; $R_5$ is hydrogen, lower alkanoyl, benzoyl, or

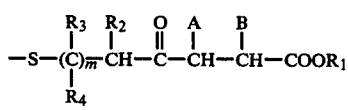

A and B each is hydrogen or join together to complete a cycloalkyl ring; m is 0 or 1; to basic salts thereof and to intermediates therefor.

The invention relates preferably to those compounds of formula I, and salts thereof, wherein A and B join to complete a cycloalkyl group, i.e., compounds of the formula

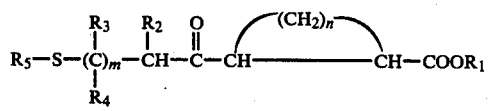

$R_1$, $R_2$, $R_3$, $R_4$, $R_5$ and m have the same meaning as above (especially when m is 1) and n is 2, 3 or 4 resulting in a cyclobutane, cyclopentane or cyclohexane ring, respectively, and to intermediates therefor.

Compounds of lesser activity and interest are the compounds of formula I, and salts thereof, wherein A and B are both hydrogen, i.e., 3-oxohexanoic or 3-oxopentanoic acid derivatives of the formula

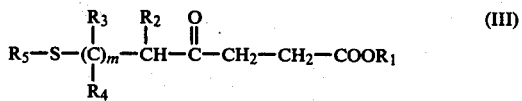

wherein the symbols have the same meaning as above.

The new intermediates which are also the subject of this invention include intermediates which are useful in preparing compounds of formula II, particularly when m is 1, i.e., intermediates which have the formula

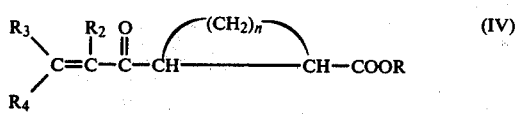

wherein $R_2$, $R_3$, $R_4$ and n have the same meaning as above and R is hydrogen, phenyl-lower alkyl or diphenyl-lower alkyl, preferably benzyl or diphenylmethyl.

DETAILED DESCRIPTION OF THE INVENTION

Especially preferred modifications are compounds of formula I wherein $R_1$, $R_2$, $R_3$ and $R_4$ are hydrogen or lower alkyl, most especially hydrogen or methyl, and primarily hydrogen; and $R_5$ is hydrogen or lower alkanoyl, most especially hydrogen or acetyl. These preferred meanings for the symbols apply to both the compounds of formula II and formula III, but as indicated above, the compounds of formula II are preferred over those of formula III.

The lower alkyl groups represented by the symbols are straight or branched chain hydrocarbon radicals having up to seven carbons like methyl, ethyl, propyl, isopropyl, butyl, isobutyl, and the like. In general, the $C_1$–$C_2$ members, are preferred.

The lower alkanoyl groups are the acyl radicals of the lower (up to seven carbon) fatty acids, e.g., acetyl, propionyl, butyryl, isobutyryl and the like. In general, the members mentioned, and especially acetyl, are preferred. The compounds of this invention can be produced by several procedures. According to one method, particularly when m is 1, an acid having the formula

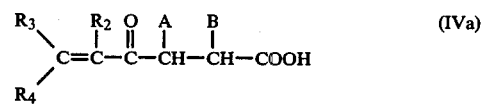

is made to react with the thiol $R_5$—SH, wherein $R_5$ is lower alkanoyl or benzoyl, to obtain the product having the formula

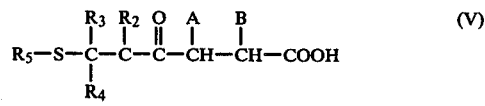

This reaction can be effected by dissolving or suspending the compound of formula IVa in an inert organic solvent such as chloroform, dichloromethane, tetrahydrofuran, dioxane, or the like, and slowly adding the thiol, preferably at a reduced temperature in the range of about 0° to 25° C. The product of formula V, wherein $R_5$ is lower alkanoyl or benzoyl, can then be converted to the corresponding product wherein $R_5$ is hydrogen, by treatment with aqueous ammonia or sodium hydroxide solution.

According to a variation of this procedure, the compound of formula IVa can be treated with the thiol as above followed directly by treatment with concentrated ammonium hydroxide solution to obtain directly the product wherein $R_5$ is hydrogen.

An alternate procedure comprises reaction of an ester of a compound of formula IVa above, e.g., phenyl-lower alkyl or diphenyl-lower alkyl ester preferably the diphenylmethyl ester, with the thiol as above, removal of the ester protection, e.g., with trifluoroacetic acid and anisole when the ester is a diphenylmethyl ester, then treatment with aqueous ammonia to remove the $R_5$ group, resulting in a product wherein $R_5$ is hydrogen.

Another procedure, particularly when m is 0, comprises utilizing an ester of the formula $$\underset{\text{HOOC—CH}\quad\text{CH}\quad\text{COO—lower alkyl}}{\overset{A\qquad B}{|\qquad|}} \quad (VI)$$

which is converted with a halogenating agent like oxalyl chloride to the acyl halide of the formula $$\underset{\text{X—C—CH—CH—COO—lower alkyl}}{\overset{O\quad A\quad B}{\|\quad|\quad|}} \quad (VII)$$

Treating this intermediate with a diazoalkane yields a diazoalkylketone of the formula $$\underset{\text{N}_2\text{C—C—CH—CH—COO—lower alkyl}}{\overset{R_2\quad O\quad A\quad B}{|\quad\|\quad|\quad|}} \quad (VIII)$$

The compound of formula VIII can then be made to react with the thiol $R_5$—SH as described above to obtain the product of formula I wherein $R_5$ is lower alkanoyl or benzoyl. Treatment of the last named product with ammonia or sodium hydroxide solution also as described above yields a product wherein $R_5$ is hydrogen.

The esters wherein $R_1$ is lower alkyl can be produced by conventional esterification methods or by utilizing an ester as starting material. They can similarly be converted to the free acid by conventional techniques such as hydrolysis, etc.

The disulfides or bis compounds wherein $R_5$ in formula I is $$-S-(C)_m-\begin{array}{c}R_3\\|\\|\\R_4\end{array}$$

are produced from a compound of formula I wherein $R_5$ is hydrogen by direct oxidation, e.g., with an alcoholic solution of iodine.

The acid of formula IVa is obtained by reacting an anhydride of the formula

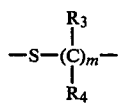

$$(IX)$$

with ethylene in the presence of a Friedel-Crafts catalyst like aluminum chloride in a solvent preferably 1,2-dichloroethane or by reacting a starting material having the formula $$\underset{\text{OHC—CH—CH—COO—lower alkyl}}{\overset{A\quad B}{|\quad|}} \quad (X)$$

with a Grignard reagent having the formula

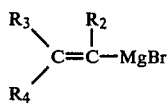

$$(XI)$$

hydrolyzing the product of this reaction with an aqueous base like sodium hydroxide to form the hydroxy acid, converting this to the diphenylmethyl ester with diphenyldiazomethane, and oxidizing the alcohol group to a keto group with chromium trioxide or manganese dioxide.

The aldehyde-esters of formula X can be produced by treating an anhydride of formula IX with methanol, reducing the acid obtained to an alcohol with diborane and oxidizing the alcohol with chromium trioxide. Alternatively, a halogenated compound of the formula $$\underset{\text{Br}_2\text{CH—CH—CH—COO—lower alkyl}}{\overset{A\quad B}{|\quad|}} \quad (XII)$$

can be converted to the compound of formula X with aqueous silver nitrate.

The compounds of formula I form basic salts with various inorganic or organic bases. They are also included in the scope of the invention. Such salts include alkali metal salts, especially the sodium and potassium salts, alkaline earth metal salts, especially calcium and magnesium salts, aluminum, dicyclohexylamine salt, benzathine salt, N-methylglucamine salt, hydrabamine salt, salts with naturally occurring amino acids like arginine, lysine and the like, lower alkylamine salts like methylamine, ethylamine, dimethylamine, triethylamine salts, etc. The non-toxic, physiologically acceptable salts are preferred, although other salts are also useful, e.g., in isolation or purifying the product as illustrated in the examples below. The salts are formed in conventional manner by reacting the free acid form of the product with one or more equivalents of the appropriate base providing the desired salt ion in a solvent or medium in which the salt is insoluble, or in water and removing the water by freeze drying. By neutralizing the salt by conventional methods the free acid form can be obtained, and if desired, another salt formed.

Additional experimental details are found in the examples which are preferred embodiments and also serve as models for the preparation of other members of the group.

The products of this invention have one or more centers of asymmetry. The compounds accordingly exist in stereoisomeric forms or in racemic mixtures thereof. All of these are within the scope of the invention.

The compounds of this invention inhibit the conversion of the decapeptide angiotensin I to angiotensin II by angiotensin converting enzyme and therefore are useful as hypotensive agents, particularly in reducing or relieving hypertension. By the administration of a composition containing one or a combination of compounds of formula I or physiologically acceptable salt thereof, angiotensin dependent hypertension in the species of mammal, e.g., rats, cats, dogs, etc., suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in conventional compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, falvor, etc., in a unit dosage form as called for by accepted pharmaceutical practice. The amount of active substance in these compositions or preparations is such that a suitable dosage in the range indicated is obtained.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty acid like ethyl oleate or the like. Buffers, preservatives, antioxidants and the like can be incorporated as required.

The following examples are illustrative of the invention and constitute especially preferred embodiments within the framework discussed above. All temperatures are in degrees Celsius.

EXAMPLE 1 cis-1,2-Cyclopentanedicarboxylic Anhydride

Method A: [cf. S. F. Birch, et al., J. Org. Chem., 20, 1178 (1955)].

A mixture of 5.0 g. (31.6 mmoles) of trans-1,2-cyclopentanedicarboxylic acid and 30 ml. of acetic anhydride is refluxed under nitrogen for eighteen hours. The acetic anhydride is removed in vacuo, and the residue distilled to give 2.75 g. of cis-1,2-cyclopentane dicarboxylic anhydride, b.p. 110°–120°/0.3 mm., which solidifies on standing. Direct recrystallization of this material from isopropyl ether/ether gives 1.8 g. of crystalline material, m.p. 50°–60°. A second recrystallization from ether affords 1.4 g. of analytically pure anhydride, m.p. 69°–72°.

Method B: [cf. Chem. Pharm. Bull., 6, 446 (1961)]

(a) 1-Cyclopentene-1,2-dicarboxylic acid

A mixture of 200 g. (1.28 moles) of ethyl-2-oxocyclopentanecarboxylate, 400 g. (430 ml., 4.50 mole) of acetone cyanohydrin, 5 g. of anhydrous potassium carbonate, and 20 drops of 10% aqueous potassium cyanide solution is stirred at room temperature overnight in the hood. The mixture is then filtered, the filtrate carefully acidified with 10% sulfuric acid to pH ~3, and insoluble material is removed by filtration. Methanol is removed from the filtrate by distillation at atmospheric pressure. Distillation of the residue affords 128.3 g. (55%) of the desired cyanohydrin, b.p. 150°–157°/8 min., which is used immediately.

The distilled cyanohydrin (128.3 g., 0.7 mole) is cooled in an ice-bath and diluted with 250 ml. of pyridine. To this cold stirred solution is added 68 ml. of phosphorus oxychloride dropwise over fortyfive minutes, and the resulting mixture left at 0°–5° for eighteen hours. The reaction mixture is heated on a steam bath for one hour, cooled and added to excess dilute hydrochloric acid-ice. This is thoroughly extracted with ether, and the combined extracts dried and concentrated in vacuo. Distillation of the residue gives 91.4 g. (79%), b.p. 118°–120°/3 mm.

A mixture of the above liquid (91.4 g., 0.55 mole) and 200 ml. of concentrated hydrochloric acid is refluxed for six hours, cooled, and the resulting precipitate is filtered off. Direct recrystallization from water (~200 ml.) (charcoal decolorization), followed by drying in vacuo over phosphorus pentoxide at 60°, affords 59.3 g. (69%) of 1-cyclopentene-1,2-dicarboxylic acid, m.p. 177°–179°.

(b) cis-1,2-Cyclopentanedicarboxylic acid

1-Cyclopentene-1,2-dicarboxylic acid (10.0 g., 0.064 mole) in 200 ml. of absolute ethanol is hydrogenated (Paar shaker) in the presence of Raney nickel at 40–50 psi/60°. After uptake of one equivalent of hydrogen (~24 hours), the mixture is cooled, filtered through a Celite (diatomaceous earth) pad, and the filtrate concentrated in vacuo to a solid. Direct recrystallization from water (~30 ml.) followed by drying in vacuo over phosphorus pentoxide yields 6 g. (60%) of cis-1,2-cyclopentanecarboxylic acid, m.p. 132°–135°. The mother liquor from the recrystallization can be lyophilized to a solid, which is sufficiently pure for use in the next step.

(c) cis-1,2-cyclopentanedicarboxylic anhydride

A mixture of 43.15 g. (0.273 mole) of the above diacid and 350 ml. of acetyl chloride is refluxed for two hours, and then taken to dryness in vacuo. Distillation of the residue gives 34.6 g. (91%) of cis-1,2-cyclopentanedicarboxylic anhydride, b.p. 100–110/0.5 mm., which crystallizes on standing.

EXAMPLE 2 cis-2-(3-Methyl-1-oxo-2-butenyl)cyclopentanecarboxylic acid

To a stirred suspension of 4.38 g. (32.86 mmole) of anhydrous aluminum chloride in 100 ml. of 1,2-dichloroethane at room temperature is added 2.30 g. (16.43 mmoles) of cis-1,2-cyclopentanedicarboxylic anhydride. Ethylene is then bubbled through the clear solution with stirring for four hours.

The solution is poured into 150 ml. of 5% aqueous hdyrochloric acid and the layers are separated. The aqueous layer is extracted with ether, the ether extracts combined with the dichloroethane solution, dried, and concentrated in vacuo. The residual oil is heated fifteen minutes on a steam bath with 25 ml. of 10% aqueous potassium carbonate, cooled, and extracted with ether. The aqueous layer is acidified with cold concentrated hydrochloric acid, and the resulting solution thoroughly extracted with ether. The combined extracts are dried and concentrated in vacuo to give 1.9 g. of oil.

The oil is taken up in chloroform, applied to a silica gel column (60 g.) and eluted with chloroform (100 ml. fractions collected). Fractions 10–15 are combined, concentrated in vacuo, and triturated with petroleum ether, yielding 0.460 g. (14.3%) of cis-2-(3-methyl-1-oxo-2-butenyl)cyclopentanecarboxylic acid, which is recrystallized from hexane, m.p. 85°–88°.

EXAMPLE 3 trans-2-[3-(Acetylthio)-1-oxopropyl]cyclohexanecarboxylic acid (a) trans-2-[1-Oxo-2-propenyl]cyclohexane carboxylic acid A mixture of aluminum chloride (66.7 g., 0.5 mole), trans-1,2-cyclohexanedicarboxylic anhydride (38.5 g., 0.25 mole) and 1,2-dichloroethane (1 liter) in a 2 liter 3-neck flask equipped with a gas inlet tube, a mechanical stirrer and a drying tube is stirred rapidly and ethylene is bubbled in for 4.5 hours. This mixture is poured into 900 ml. of 5% hydrochloric acid and ice. The layers are separated and the organic layer is washed with water and taken to dryness in vacuo. The aqueous layer is extracted with ether (300 ml.). This extract is washed with water and combined with material from the original organic layer and taken to dryness. The residue is heated with 300 ml. of 10% potassium carbonate on a steam bath for fifteen minutes. After cooling, the mixture is extracted three times with ether. The aqueous layer is acidified and the product trans-2-[1-oxo-2-propenyl]cyclohexanecarboxylic acid (31.6 g.) is extracted into ether, dried and concentrated in vacuo. The crude crystalline trans-2-(1-oxo-2-propenyl)cyclohexanecarboxylic acid is recrystallized from ether-hexane, m.p. 101°–102°.

(b) trans-2-[3-(Acetylthio)-1-oxopropyl]-cyclohexanecarboxylic acid

The crude olefinic acid obtained above (22 g.) is dissolved in 100 ml. of chloroform and while cooling slightly and stirring, 15 ml. (0.21 M) of thiolacetic acid is added dropwise over a period of ten minutes. After stirring one hour at room temperature, the mixture is taken to dryness in vacuo leaving a yellow rubbery material. This is dissolved in chloroform and chromatographed on silica gel (1 lb.), eluting with chloroform, to give 17 g. of oil which crystallizes on trituration with hexane. A 3.0 sample is recrystallized from isopropyl ether to give 1.7 g. of trans-2-[3-(acetylthio)-1-oxopropyl]-cyclohexanecarboxylic acid, m.p. 65°–68°.

EXAMPLE 4 trans-2-(3-Mercapto-1-oxopropyl)cyclohexanecarboxylic acid trans-2-[3-(Acetylthio)-1-oxopropyl]cyclohexanecarboxylic acid (3.0 g., 11.6 mmol.) is added to a cold mixture of 5 ml. of concentrated ammonium hydroxide and 5 ml. of water under argon. The mixture is stirred at room temperature for 30 minutes. While cooling to 0°, the solution is acidified with concentrated hydrochloric acid. The mixture is extracted four times with ethyl acetate. The extracts are dried and the solvent is removed in vacuo. The oily product is chromatographed on 90 g. of silica gel eluting with ethyl acetate. A total of 2.2 g. (88%) of material is obtained which is contaminated with some more polar material. Chromatography of 1.9 g. of this material on 60 g. of silica gel and eluting with chloroform and 2% methanol in chloroform gives 1.4 g. of trans-2-(3-mercapto-1-oxopropyl)cyclohexanecarboxylic acid, recrystallized from isopropyl ether-hexane, 1.0 g. (46%), m.p. 71°–74°.

EXAMPLE 5 cis-2-[3-(Acetylthio)-1-oxopropyl]cyclohexanecarboxylic acid (a) cis-2-[1-Oxo-2-propenyl]cyclohexanecarboxylic acid A mixture of 66.7 g. (0.5 mole) of anhydrous aluminum chloride and 38.5 g. (0.25 mole) of freshly distilled cis-1,2-cyclohexanedicarboxylic anhydride in 1 liter of 1,2-dichloroethane is stirred vigorously while bubbling in ethylene for 4.5 hours. The mixture is then poured into 900 ml. of 5% aqueous hydrochloric acid and ice. The layers are separated and the organic layer is washed with water and taken to dryness in vacuo. The aqueous layer is extracted with 300 ml. of ether, the extract is washed with water and then combined with material from the original organic layer and taken to dryness in vacuo.

The residue is heated with 150 ml. of 10% aqueous potassium carbonate solution on a steam bath for 15 minutes. After cooling, the mixture is extracted with ether. The aqueous layer is acidified, and the product cis-2-[1-oxo-2-propenyl]cyclohexanecarboxylic acid is extracted into ether.

The original ether extracts are extracted with 150 ml. of 10% aqueous potassium carbonate. This aqueous layer is then acidified with dilute aqueous hydrochloric acid and the product is extracted into ether. After drying and concentration in vacuo, 23.4 g. of viscous foam is obtained and used without further purification.

(b) cis-2-[3-(Acetylthio)-1-oxopropyl]-cyclohexanecarboxylic acid, dicyclohexylamine salt To a stirred solution of 22 g. of the above crude foam in 100 ml. of chloroform at 0°–5° is added dropwise 15 ml. of thiolacetic acid. After the addition is complete, the solution is left at 0°–5° for one hour, and then taken to dryness in vacuo.

The residue is taken up in chloroform and applied to a silica gel column (450 g.) and eluted as follows:

| Fractions | Size | Solvent |
| --- | --- | --- |
| 1–2 | 500 ml. | CHCl$_3$ |
| 3–18 | 200 ml. | CHCl$_3$ |
| 19–21 | 200 ml. | 1% MeOH/CHCl$_3$ |
| 22–35 | 200 ml. | 5% MeOH/CHCl$_3$ |

Fractions 30–32 are combined, treated with hot isopropyl ether, filtered to remove polymeric material, and the filtrate concentrated in vacuo. The resulting oil is taken up in ether (total volume=200 ml.) and treated with 10 ml. of dicyclohexylamine. The resulting crystalline solid dicyclohexylamine salt is filtered off, washed with ether, and dried in vacuo to give 9.45 g., m.p. 134°–138°.

(c) cis-2-[3-(Acetylthio)-1-oxopropyl]-cyclohexanecarboxylic acid

A suspension of 2.0 (4.5 mmole) of the dicyclohexylamine salt from part b in ethyl acetate is treated with excess 10% aqueous potassium bisulfate and the layers separated. The aqueous layer is extracted with ethyl acetate, and the combined organic layers dried and concentrated in vacuo to give 1.35 g. of oil. Trituration of 1.2 g. of this oil with petroleum ether gives 0.80 g. (69%) of cis-2-[3-(acetylthio)-1-oxopropyl]cyclohexanecarboxylic acid which is recrystallized from isopropyl ether, m.p. 79°–81°.

EXAMPLE 6

L-cis-2-(3-Mercapto-1-oxopropyl)cyclohexanecarboxylic acid

A solution of 2.5 g. (9.68 mmoles) of cis-2-[3-(acetylthio)-1-oxopropyl]cyclohexanecarboxylic acid in 5 ml. of concentrated ammonium hydroxide and 5 ml. of water is kept at 0°–5° for one hour. The cold reaction mixture is then acidified with cold concentrated hydrochloric acid and thoroughly extracted with ethyl acetate. The combined extracts are dried and concentrated in vacuo to 2.3 g. of oil. This oil is taken up in chloroform and applied to a silica gel column (60 g.) and eluted as follows:

| Fractions | Size | Solvent |
| --- | --- | --- |
| 1–5 | 50 ml. | $CHCl_3$ |
| 6–15 | 50 ml. | 2% $MeOH/CHCl_3$ |

Fractions 6–13 give a solid on trituration with hexane. The solids are combined (total=1.5 g.=72%) and recrystallized from isopropyl ether/hexane to give L-cis-2-(3-mercapto-1-oxopropyl)cyclohexanecarboxylic acid (1.1 g.), m.p. 82.5°–84.5°.

EXAMPLE 7 trans-2-[3-(Acetylthio)-2-methyl-1-oxopropyl]cyclohexanecarboxylic acid (Isomer A)

(a) trans-1,2-Cyclohexanedicarboxylic acid, monomethyl ester

A mixture of 53.3 g. (0.346 mole) of trans-1,2-cyclohexanedicarboxylic anhydride and 75 ml. of methanol is heated under reflux for two hours. After cooling the methanol is removed in vacuo. The residue is treated with hexane and crystalline material is deposited. This is harvested and washed with more hexane to give 58.2 g. (90%) of trans-1,2-cyclohexanedicarboxylic acid, monomethyl ester, m.p. 93°–97° [cf. J. Amer. Chem Soc. 72, 4406 (1950)].

(b) trans-2-(Hydroxymethyl)cyclohexanecarboxylic acid, methyl ester

A solution of 18.6 g. (0.1 mole) of the acid ester from part a in 50 ml. of dry tetrahydrofuran under nitrogen is treated dropwise over a period of one hour with 100 ml. of 1 M borane solution (in tetrahydrofuran) maintaining the temperature at 20°–30° with intermittent cooling. After addition is complete, the mixture is stirred at room temperature for one hour. Water is added dropwise to decompose any excess borane. The solvent is removed in vacuo. Water is added to the residue and the product trans-2-(hydroxymethyl)cyclohexanecarboxylic acid, methyl ester is extracted into ether. After drying and removal of solvent 16.8 g. (98%) of product remains as an oil.

(c) trans-2-Formylcyclohexanecarboxylic acid, methyl ester

Chromium trioxide (60 g., 0.6 mole) is added to a mechanically stirred cooled solution of 95 g. (1.2 mole) of pyridine in 1.5 liters of methylene chloride. The mixture is stirred at room temperature for twenty minutes. A solution of 16.8 g. (0.098 mole) of the product of part b in 100 ml. of methylene chloride is added. The mixture is stirred at room temperature for twenty minutes. The solution is decanted from the dark gummy material on the side of the flask. A small amount of methylene chloride is used as a wash. The solvent is removed from the decanted solution in vacuo. Ether is added to the residue. Chromium salts are removed by filtration through diatomaceous earth. The solvent is removed in vacuo leaving 15.2 g. (91%) of trans-2-formylcyclohexanecarboxylic acid, methyl ester as a reddish oil.

(d) trans-2-(1-Hydroxy-2-methyl-2-propenyl)-cyclohexane carboxylic acid

The Grignard reagent of 2-bromopropene is prepared in tetrahydrofuran using 2.19 g. (0.09 mole) of magnesium and 12.1 g. (0.1 mole) of 2-bromopropene. This is added dropwise over thirty-five minutes to a cooled (0°–5°) stirred solution of 15.2 g. (0.09 mole) of the crude aldehyde from part c in 125 ml. of tetrahydrofuran. Stirring and cooling is continued for fifteen minutes after addition is complete. Saturated aqueous ammonium chloride solution (~ 100 ml.) is then added dropwise. The layers are separated and the aqueous portion is reextracted with ether. The combined organic layers are washed twice with saturated salt solution, dried and the solvent is removed in vacuo leaving 12.8 g. (79%) of oil which is chromatographed on one pound of silica gel, eluting with benzene and 20% chloroform in benzene. Fractions appearing clean on thin layer chromatography are combined to give 7.2 g. of oily addition product.

The above oil (5.2 g., 29 mmole) and 29 ml. 1 N sodium hydroxide are heated under reflux under nitrogen for ninety minutes. After cooling, the solution is extracted twice with ethyl acetate to remove any neutral material. The aqueous layer is acidified with cold 10% potassium bisulfate solution while under a layer of ethyl acetate. The layers are separated and the aqueous portion is extracted two more times with ethyl acetate. The combined organic layers are dried, filtered, and freed of solvent in vacuo leaving 5.5 g. (96%) of largely crystalline product, trans-2-(1-hydroxy-2-methyl-2-propenyl)-cyclohexane carboxylic acid. The material is used immediately.

(e) trans-2-(1-Hydroxy-2-methyl-2-propenyl)-cyclohexanecarboxylic acid, diphenylmethyl ester The olefinic hydroxy acid from part d (5.5 g., 27.7 mmoles) is partially dissolved in 100 ml. ethyl acetate. While stirring under nitrogen, diphenyldiazomethane (5.4 g., 27.7 mmol.) is added portionwise over a period of thirty minutes. The mixture is stirred overnight at room temperature. The solution is washed twice with saturated sodium bicarbonate solution, dried and freed of solvent in vacuo to give crude ester, trans-2-(1-hydroxy-2-methyl-2-propenyl)-cyclohexanecarboxylic acid, diphenylmethyl ester, as a reddish oil, 9.8 g. (97%).

(f) trans-2-(2-Methyl-1-oxo-2-propenyl)cyclohexanecarboxylic acid, diphenylmethyl ester Chromium trioxide (24 g., 240 mmoles) is added to a cooled stirred solution of 38 g. (480 mmoles) of pyridine in 600 ml. of methylene chloride. The mixture is stirred at room temperature for twenty minutes. A solution of 9.8 g. (27 mmol.) of the ester from part e in a small amount of methylene chloride is added and stirring is continued for twenty minutes. The solution is then decanted from the dark gummy residue. A small amount of methylene chloride is used to wash the residue and combined with the original decanted solution. This is taken to dryness in vacuo. Ether is added and filtered through diatomaceous earth to remove chromium salts. The solvent is removed in vacuo leaving 8.4 g. partially crystalline product trans-2-(1-oxo-2-methyl-2-propenyl)cyclohexanecarboxylic acid, diphenylmethyl ester which is recrystallized from hexane (150 ml.) to give 4.5 g. (46%), m.p. 90°-95°.

A portion (0.5 g.) is recrystallized from hexane to give an analytical sample (450 mg.), m.p. 92°-94°.

(g)
trans-2-[3-(Acetylthio)-2-methyl-1-oxopropyl]cyclohexanecarboxylic acid, diphenylmethyl ester The crystalline material from part f (4.0 g., 11 mmoles) is dissolved in 40 ml. of methylene chloride. Thiolacetic acid (4.5 ml.) is added and the solution is stirred at room temperature for two hours. The solvent is removed in vacuo to leave an oil. This is dissolved in benzene and chromatographed on 250 g. of silica gel. After eluting trace amounts of impurities with benzene and benzene-chloroform (1:1), the product trans-2-[3-(acetylthio)-2-methyl-1-oxopropyl]cyclohexanecarboxylic acid, diphenylmethyl ester 4.7 g. (97%) is eluted as an oil.

(h)
trans-2-[3-(Acetylthio)-2-methyl-1-oxopropyl]cyclohexanecarboxylic acid (Isomer A)

The chromatographed compound of part g (4.7 g., 10.7 mmol.) and anisole (21.6 g., 200 mmoles) is cooled to 0° under nitrogen. Trifluoroacetic acid (60 ml.) is added dropwise over a period of sixty minutes while stirring and cooling. After cooling an additional sixty minutes, the trifluoroacetic acid is removed in vacuo. Ether is added and the product is extracted three times into saturated sodium bicarbonate solution. The combined aqueous layer is washed twice with ether and then acidified with hydrochloric acid. The product is extracted into ether, dried and taken to dryness in vacuo leaving 3.0 g. of oil. The NMR of this material shows two sharp peaks for the S-acetylmethyl groups indicating a mixture of isomers. This is crystallized from isopropyl ether/hexane to give 1.3 g. of material enriched in trans-2-[3-(acetylthio)-2-methyl-1-oxopropyl]cyclohexanecarboxylic acid, isomer A. The mother liquor is taken to dryness to give 1.1 g. of oil, very much enriched in isomer B and is used in Example 9. The crystalline material is recrystallized from isopropyl ether-hexane to give 700 mg. (24%) of trans-2-[3-(acetylthio)-2-methyl-1-oxopropyl]-cyclohexanecarboxylic acid, which NMR indicates is a single isomer (A), m.p. 103°-108°.

EXAMPLE 8 trans-2-(3-Mercapto-2-methyl-1-oxopropyl)cyclohexanecarboxylic acid (Isomer A)

The crystalline trans-2-[3-(acetylthio)-2-methyl-1-oxopropyl]cyclohexanecarboxylic acid, Isomer A from part h, Example 7 (680 mg., 2.5 mmoles) is added to a cold mixture of 1.5 ml. concentrated ammonium hydroxide and 1.5 ml. water under argon. The mixture is stirred at room temperature for thirty minutes, then cooled and acidified with hydrochloric acid. The product is extracted into ethyl acetate, dried and freed of solvent in vacuo leaving a yellow oil which crystallizes on standing. This material is dissolved in chloroform and chromatographed on 15 g. of silica gel. The product is eluted with 2% methanol in chloroform. Fractions giving strong sulfhydryl positive test with sodium nitroprusside spray and appearing clean on thin layer chromatography (silica gel, developed with ethyl acetate) are pooled and freed of solvent in vacuo to give 500 mg. of crystalline trans-2-(3-mercapto-2-methyl-1-oxopropyl)cyclohexanecarboxylic acid which is recrystallized from isopropyl ether (~ 3 ml.) to give 230 mg. (40%) of very dense white crystalline material, m.p. 87°-90°.

EXAMPLE 9 trans-2-(3-Mercapto-2-methyl-1-oxopropyl)cyclohexanecarboxylic acid (Isomer B)

The mother liquor from the first crystallization of trans-2-[3-(acetylthio)-2methyl-1-oxopropyl]cyclohexanecarboxylic acid in Example 7 is taken to dryness and found by NMR to be nearly clean isomer B. This oil (900 mg., 3.3 mmoles) is treated with a cold mixture of 2 ml. of concentrated ammonium hydroxide and 2 ml. of water in an argon atmosphere. After stirring thirty minutes at room temperature, the mixture is washed once with ether. The aqueous layer is cooled and acidified with hydrochloric acid. The product is extracted into ethyl acetate, dried and freed of solvent in vacuo leaving 0.65 g. of material which is largely crystalline. This is dissolved in chloroform and chromatographed on 20 g. silica gel. The product is eluted with 2% methanol in chloroform. Fractions appearing clean on TLC (silica gel, EtOAc or 10% MeOH in $CHCl_3$, detected with sodium nitroprusside spray) are combined to give 550 mg. (~ 72%) of crystalline material. Recrystallization from ~ 2 ml. isopropyl ether gives 165 ml. (22%) of fluffy white crystalline trans-2-(3-mercapto-2-methyl-1-oxopropyl)cyclohexanecarboxylic acid, m.p. 91°-93°.

EXAMPLE 10 cis-2-(3-Mercapto-3-methyl-1-oxobutyl)cyclopentanecarboxylic acid

A solution of 600 mg. (3.06 mmoles) of crude cis-2-(3-methyl-1-oxo-2-propenyl)cyclopentanecarboxylic acid in 5 ml. of chloroform is treated with 1 ml. of thiolacetic acid and left at room temperature for sixty-four hours. The solution is concentrated in vacuo to an oil, which is taken up in chloroform, applied to a silica gel column, and eluted with chloroform (50 ml. fractions collected). Fractions eight and nine afford 437 mg. (50%) of cis-2-(3-acetylthio-3-methyl-1-oxobutyl)cyclopentanecarboxylic acid as an oil.

The oil is stirred thirty minutes at room temperature in a mixture of 1 ml. each of water and concentrated ammonium hydroxide. The solution is cooled, acidified with dilute hydrochloric acid and thoroughly extracted with ethyl acetate. The combined extracts are dried and concentrated in vacuo to 277 mg. (74%) of oil. The oil is taken up in chloroform and applied to a preparative TLC plate (silica gel, 20×20 cm., 2 mm, 5% MeOH/$CHCl_3$). The major band ($R_f=0.4$) is extracted with hot ethyl acetate, affording 140 mg. of oil. The oil is taken up in 5 ml. of ether and treated with 0.2 ml. of dicyclohexylamine, affording 73 mg. of dicyclohexylamine salt, m.p. 127°–130°.

The dicyclohexylamine salt is converted into the free acid by treatment with 10% aqueous potassium bisulfate and extraction with ethyl acetate, affording 31 mg. of low melting solid cis-2-(3-mercapto-3-methyl-1-oxobutyl)cyclopentanecarboxylic acid.

The potassium salt is obtained by treating the oil with potassium hydroxide solution and lyophylizing.

EXAMPLE 11 trans-2-[3-(Acetylthio)-1-oxopropyl]cyclopentanecarboxylic acid (a) trans-2-Formylcyclopentanecarboxylic acid, methyl ester A solution of 25 g. (83.3 mmoles) of trans-2-dibromomethyl-1-cyclopentanecarboxylic acid, methyl ester [prepared as described in Chem. Ber. 110, 1823 (1977), from cyclopentene and dibromoketene] in 140 ml. of tetrahydrofuran is heated to reflux in a nitrogen atmosphere. While stirring, a solution of 33.0 g. (194 mmole) of silver nitrate in 55 ml. of water is added over a period of ten minutes. After an additional thirty minutes of heating and stirring the mixture is cooled and saturated aqueous sodium chloride solution is added. The mixture is then neutralized with saturated aqueous sodium carbonate solution and the insoluble salts are removed by filtration through a Celite (diatomaceous earth) pad. The pad is washed with ether and some solid sodium chloride is added to the filtrate. The layers are separated and the aqueous portion is reextracted twice with ether. The combined organic layers are dried over magnesium sulfate, filtered and taken to dryness in vacuo leaving 7.5 g. of amber oil. This is distilled at reduced pressure collecting 4.1 g. (32%) of product, trans-2-formylcyclopentanecarboxylic acid, methyl ester, boiling at 60°–85°/0.4 mm.

(b) trans-2-(1-Hydroxy-2-propenyl)cyclopentanecarboxylic acid

The Grignard reagent of vinyl bromide is prepared in tetrahydrofuran using 0.39 g. (16 mmoles) of magnesium and 2.5 g. of vinyl bromide. This is added dropwise over thirty minutes to a cooled (0°–5°), stirred solution of 2.5 g. (16 mmol.) of distilled aldehyde from part a in 20 ml. of tetrahydrofuran. Stirring and cooling is continued for fifteen minutes after addition is complete. Saturated aqueous ammonium chloride solution (20 ml.) is then added dropwise. The layers are separated and the aqueous layer is reextracted with ether. The combined organic layers are washed twice with saturated sodium chloride solution, dried and the solvent is removed in vacuo leaving 2.3 g. of trans-2-(1-hydroxy-2-propenyl)cyclopentanecarboxylic acid as a yellow oil.

The oil including a small amount of the corresponding lactone is added to 18 ml. of 1 N sodium hydroxide and heated under reflux in a nitrogen atmosphere for 1.5 hours. After cooling, the solution is extracted twice with ethyl acetate to remove any neutral material. The aqueous layer is acidified with cold 10% potassium bisulfate solution. The product is extracted into ethyl acetate, dried and freed of solvent leaving 2.0 g. (73%) of product.

(c) trans-2-(1-Hydroxy-2-propenyl)cyclopentanecarboxylic acid, diphenylmethyl ester The material obtained in part b (2.0 g., 11.7 mmoles) is dissolved in 50 ml. of ethyl acetate. While stirring under nitrogen, diphenyldiazomethane (2.2 g., ~11.5 mmol.) is added in several portions over a period of thirty minutes. The mixture is stirred overnight at room temperature. The solution is washed twice with saturated sodium bicarbonate solution, dried and freed of solvent in vacuo leaving 3.65 g. of reddish viscous oil. The oil is dissolved in chloroform and chromatographed on a 100 g. silica gel column using chloroform to elute. Fractions appearing clean on TLC are combined and taken to dryness in vacuo leaving 1.35 g. (35%) of trans-2-(1-hydroxy-2-propenyl)cyclopentanecarboxylic acid, diphenylmethyl ester as an oil.

(d) trans-2-(1-Oxo-2-propenyl)cyclopentanecarboxylic acid, diphenylmethyl ester

The oil obtained in part d (1.35 g., 4.0 mmoles) is dissolved in 60 ml. of methylene chloride and 13 g. activated manganese dioxide are added and stirred overnight under argon. The manganese dioxide is removed by filtration. The filtrate is taken to dryness leaving 1.0 g. of yellow oil. This is chromatographed on 25 g. of silica gel using benzene to elute. Fractions appearing nearly clean on TLC are combined and taken to dryness in vacuo leaving 0.7 g. (52%) of trans-2-(1-oxo-2-propenyl)cyclopentanecarboxylic acid, diphenylmethyl ester as a yellow oil.

(e) trans-2-[3-(Acetylthio)-1-oxopropyl]cyclopentanecarboxylic acid, diphenylmethyl ester The oil obtained in part d (0.7 g., 2.1 mmoles) is dissolved in 10 ml. chloroform and 0.7 ml. of thiolacetic acid is added. After stirring one hour at room temperature, the mixture is taken to dryness in vacuo leaving 0.8 g. of pale yellow oil. This is chromatographed on 25 g. of silica gel using benzene to elute. Fractions appearing clean on TLC are combined and taken to dryness in vacuo leaving 625 mg. (72%) of trans-2-[3-(acetylthio)-1-oxopropyl]cyclopentanecarboxylic acid, diphenylmethyl ester as an oil.

(f) trans-2-[3-(Acetylthio)-1-oxopropyl]cyclopentanecarboxylic acid

The oil obtained in part e, (625 mg. ~1.5 mmoles) in 3.25 g. (30 mmoles) of anisole is stirred and cooled (0°–5°) in a nitrogen atmosphere and 10 ml. of trifluoroacetic acid are added dropwise over a period of forty minutes. After addition is complete the mixture is stirred with cooling for an additional sixty minutes. The trifluoroacetic acid is removed in vacuo. The residue is dissolved in ether and extracted three times with saturated sodium bicarbonate solution. The combined aqueous layers are washed twice with ether to remove any neutral material. The aqueous portion is then acidified with hydrochloric acid and extracted three times with ether. These ether extracts are dried ($MgSO_4$), filtered and the solvent is removed in vacuo leaving 400 mg. (quantitative) of trans-2-[3-(acetylthio)-1-oxopropyl]cyclopentanecarboxylic acid as a yellow oil. TLC (silica gel, 10% MeOH in $CHCl_3$, $I_2$) shows a major spot at $R_f=0.55$.

EXAMPLE 12 trans-2-(3-Mercapto-1-oxopropyl)cyclopentanecarboxylic acid

A cold argon saturated mixture of 1 ml. concentrated ammonium hydroxide and 1 ml. of water is added to trans-2-[3-(acetylthio)-1-oxopropyl]-cyclopentanecarboxylic acid (1.5 mmoles) swirled at room temperature for thirty minutes, cooled and then acidified with concentrated hydrochloric acid. This is extracted three times with ethyl acetate. The combined ethyl acetate extracts are dried, filtered and the solvent is removed in vacuo leaving ~350 mg. which is dissolved in chloroform and spotted on a 20×20 cm. preparative silica gel plate. The plate is developed in 10% methanol in chloroform. Detecting by UV, the band corresponding to a spot giving a positive SH test on an analytical plate is removed and eluted with warm ethyl acetate. The ethyl acetate solution is washed twice with water, dried and taken to dryness in vacuo leaving 135.7 mg. (45%) of trans-2-(3-mercapto-1-oxopropyl)cyclopentanecarboxylic acid as a yellow oil.

This oil (0.67 mmol.) is dissolved in a small amount of isopropyl ether and converted to the dicyclohexylamine salt by adding a slight excess of dicyclohexylamine. Crystalline material (202 mg.) is harvested and recrystallized from isopropyl ether to give trans-2-(3-mercapto-1-oxopropyl)cyclopentanecarboxylic acid, dicyclohexylamine salt (171 mg., 67%) m.p. 126°–128°.

The bulk of the salt (150 mg., 0.39 mmol.) is reconverted to the free acid with 10% potassium bisulfate solution. The acid is extracted into ethyl acetate, dried and freed of solvent in vacuo to give 74.4 mg. of the acid (94%) as an oil. TLC (silica gel, 10% MeOH in CHCl$_3$, detected SH spray and I$_2$), large major spot (SH positive) R$_f$=0.41.

EXAMPLE 13 cis-2-[3-(Acetylthio)-1-oxopropyl]cyclobutanecarboxylic acid (a) cis-2-[1-Oxo-2-propenyl]cyclobutanecarboxylic acid A mixture of aluminum chloride (66.7 g., 0.5 M), 1,2-cyclobutanedicarboxylic anhydride (31.5 g., 0.24 M) and 1,2-dichloroethane (1 liter) in a 2 liter 3-neck flask equipped with a gas inlet tube, a mechanical stirrer and a drying tube is stirred rapidly and ethylene is bubbled in for 4.5 hours. This mixture is poured into 900 ml. 5% hydrochloric acid and ice. The layers are separated and the organic layer is washed with water and taken to dryness in vacuo. The aqueous layer is extracted with ether (300 ml.). The extract is washed with water and combined with material from the original organic layer and taken to dryness. The residue is heated with 150 ml. of 10% potassium carbonate on a steam bath for fifteen minutes. After cooling the mixture is extracted three times with ether. The aqueous portion is acidified and the product (1.5 g.) is extracted into ether. The original ether extracts are combined and extracted with 150 ml. of 10% potassium carbonate solution. This aqueous layer is then acidified with hydrochloric acid and the product cis-2-[1-oxo-2-propenyl]cyclobutanecarboxylic acid (24.3 g.) is extracted into ether. Both samples (25.8 g., 67%) crystallize on standing.

(b) cis-2-[3-(Acetylthio)-1-oxopropyl]cyclobutanecarboxylic acid

The crude acid obtained in part a (24.3 g., 0.16 M) is dissolved in 100 ml. of chloroform. The solution is cooled in an ice bath and 15 ml. (~0.21 M) of thiolacetic acid is added dropwise over a period of twenty minutes. After stirring one hour at room temperature, the mixture is taken to dryness in vacuo leaving a viscous oil (36 g.). This is dissolved in chloroform and chromatographed on 1 pound of silica gel to give material which crystallizes on trituration with hexane. The crystalline material (10.6 g., 29%) is recrystallized from isopropyl ether to give cis-2-[3-(acetylthio)-1-oxopropyl]cyclobutanecarboxylic acid, 6.6 g., m.p. 50°–54°.

EXAMPLE 14 cis-2-(3-Mercapto-1-oxopropyl)cyclobutanecarboxylic acid cis-2-[3-(Acetylthio)-1-oxopropyl]cyclobutanecarboxylic acid (2.5 g., 10.9 mmol.) is added to a cold mixture of 5 ml. of concentrated ammonium hydroxide and 5 ml. of water in an argon atmosphere. The solution is stirred at room temperature for thirty minutes. While cooling, the mixture is acidified with hydrochloric acid and the product is extracted into ethyl acetate, dried, and freed of solvent in vacuo leaving 2.1 g. of oil. This is chromatographed on 50 g. of silica gel eluting with chloroform and 2% methanol in chloroform. The oil obtained (clean by TLC, silica gel, 10% methanol in chloroform—R$_f$=0.43) (1.35 g., 66%) is dissolved in ether and converted to cis-2-(3-mercapto-1-oxopropyl)cyclobutanecarboxylic acid, dicyclohexylamine salt, by adding a slight excess of dicyclohexylamine. The white solid is recrystallized from ethyl acetate to give 2.0 g., m.p. 129°–132°.

The salt is converted to the free acid with 10% potassium bisulfate solution and extracted into ethyl acetate to give 0.95 g. of cis-2-(3-mercapto-1-oxopropyl)cyclobutanecarboxylic acid as an oil.

EXAMPLE 15 trans-2-(3-Mercapto-1-oxopropyl)cyclobutane carboxylic acid

A solution of 460 mg. (2 mmol.) cis-2-[3-(acetylthio)-1-oxopropyl]cyclobutanecarboxylic acid in 10 ml. of methanol is cooled to 0° in an argon atmosphere and 324 mg. (6 mmol.) of sodium methoxide is added. The mixture is stirred at 0° for two hours and then acidified with 2 N hydrochloric acid. The methanol is removed in vacuo. Water is added and the product is extracted into ethyl acetate to give 320 mg. of an oil. This is purified on a preparative TLC plate (silica gel, developed 10% MeOH in CHCl$_3$). The band containing product is scraped off and eluted with ethyl acetate to give 150 mg. of oil (40%). This oil is dissolved in ether and converted to the dicyclohexylamine salt by adding a slight excess of dicyclohexylamine. The white solid is recrystallized from ethyl acetate to give 250 mg. of trans-2-(3-mercapto-1-oxopropyl)cyclobutanecarboxylic acid, dicyclohexylamine salt, m.p. 140°–144°.

The salt is converted to the free acid with 10% potassium bisulfate solution. The acid is extracted into ethyl acetate, dried, and freed of solvent leaving trans-2-(3-mercapto-1-oxopropyl)cyclobutanecarboxylic acid as an oil (120 mg.) which is dissolved in water containing a few drops of ethanol and lyophillized.

The sodium salt is obtained from the oil by adding an equivalent amount of sodium hydroxide solution then lyophilizing.

EXAMPLE 16

6-(Acetylthio)-4-oxohexanoic acid (a) 4-Oxo-5-hexenoic acid

[cf. J. Chem. Soc., 3922 (1958)]. A mixture of aluminum chloride (66.7 g., 0.5 M), succinic anhydride (25 g., 0.25 M) and 1,2-dichloroethane (1 liter) in a 2 liter 3 neck flask equipped with a gas inlet tube, a mechanical stirrer and a drying tube is stirred rapidly and ethylene is bubbled in for 4.5 hours. This is poured into 900 ml. 5% hydrochlorc acid and ice. The layers are separated and the organic layer is washed with water and taken to dryness in vacuo. The aqueous layer is extracted with ether (300 ml.). This extract is washed with water and combined with the material from the original organic layer. After removal of solvent, 150 ml. of 10% potassium carbonate solution is added and the mixture is heated on a steam cone for 15 minute. After cooling, the product 4-oxo-5-hexenoic acid is extracted into ether, dried and freed of solvent in vacuo leaving 10.9 g. (34%) of brownish liquid which solidifies on standing. This is distilled to give 7.1 g. (22%) of colorless liquid which solidifies on standing, b.p. ~120°–130°/0.5 mm.

(b) 6-(Acetylthio)-4-oxohexanoic acid

The distilled 4-oxo-5-hexenoic acid (6.8 g., 58 mmol.) from part a is dissolved in 30 ml. of methylene chloride. Thiolacetic acid (4.0 g., 65 mmol.) is added dropwise. After stirring at room temperature 45 minutes, a very small amount of insoluble material is removed by filtration. The solvent is removed in vacuo leaving 9.9 g. (84%) of near white solid. Petroleum ether is added and the crystalline material is harvested by filtration. This is recrystallized from benzene to give 6-(acetylthio)-4-oxohexanoic acid, 6.2 g. (52%), m.p. 72°–74°.

EXAMPLE 17

6-Mercapto-4-oxohexanoic acid 6-(Acetylthio)-4-oxohexanoic acid (3.5 g., 17 mmol.) is added to a cold solution of 5 ml. of concentrated ammonium hydroxide and 5 ml. of water under argon. The solution is stirred at room temperature for 30 minutes. While cooling in an ice-bath, the mixture is acidified with concentrated hydrochloric acid. The mixture is continuously extracted with ethyl acetate for 24 hours to give a total of 3.6 g. of extracted material, largely oil but containing some crystalline material. Trituration with ether gives 240 mg. of solid material.

The ether soluble portion of the ethyl acetate extract is taken to dryness and chromatographed on 90 g. of silica gel using chloroform as the eluant. The crystalline material obtained (1.6 g., 58%) is recrystallized from ether-hexane to give 6-mercapto-4-oxohexanoic acid, 850, g. (31%), m.p. 40°–42°.

The sodium salt is formed as in Example 15.

EXAMPLE 18 trans-2-(Mercaptoacetyl)cyclohexanecarboxylic acid (a) trans-1,2-Cyclohexanedicarboxylic acid, monomethyl ester is prepared as described in Example 7a.

This is converted to the acid chloride by dissolving 7.4 g. (40 mmol.) in 100 ml. ether and treating with 4 ml. of oxalyl chloride and a few drops of dimethylformamide. The solution is stirred ninety minutes at room temperature and the solvent is removed in vacuo without heating. The acid chloride is dissolved in 200 ml. of ether, cooled in an ice bath and treated with an ether solution of diazomethane (prepared from 20 g. N-methyl-N'-nitro-N-nitrosoquanidine). The solution is stirred with cooling for two hours, and one hour and fifteen minutes at room temperature. A very small amount of insoluble mateial is removed by filtration. The filtrate is washed once with saturated sodium bicarbonate solution and once with saturated sodium chloride solution, dried and freed of solvent in vacuo leaving 7.4 g. (88%) of material which solidifies on standing.

(b) The diazomethylketone obtained in part a (7.4 g., 35.2 mmol.) is dissolved in 70 ml. of chloroform and 10.5 ml. thiolacetic acid.

After standing for four days at room temperature, the solvent is removed in vacuo leaving 9.1 g. of yellow oil. The material is dissolved in benzene and chromatographed on 200 g. of silica gel. After removal of the contaminants with benzene and mixtures of benzene and chloroform, the desired 2-(acetylthio)cyclohexane carboxylic acid is eluted eith chloroform. Fractions appearing clean by TLC are combined to give 2.15 (24%) of material as an oil. Another pool of fractions (2.5 g.) contaminated with an appreciable amount of slower moving material is set aside.

(c) Chromatographed S-acetyl compound from part b (2.6 g., 10 mmol.) is treated with 50 ml. of 1 N sodium hydroxide which has been saturated with argon and the mixture is stirred overnight under argon.

After extracting twice with ether to remove any non-acidic material, the aqueous solution is cooled and acidified with hydrochloric acid. The product is extracted into ethyl acetate, dried and freed of solvent in vacuo to give 2.1 g. of yellow oil. The oil is dissolved in chloroform and chromatographed on 60 g. of silica gel, eluting with chloroform. Fractions giving strong positive reaction with SH spray are checked on TLC and the fractions appearing clean are combined and taken to dryness to give 900 mg. (44%) of crystalline material. This is recrystallized from isopropyl ether with a charcoal decolorization to give trans-2-(mercaptoacetyl)cyclohexanecarboxylic acid, 618 mg. (30%), shrinking 102°, m.p. 112°–117°.

EXAMPLE 19

(trans)-2,2'-[Dithiobis(1-oxo-3,1-propanediyl)]biscyclohexanecarboxylic acid 3.0 g. (13.89 mmole) trans-2-(3-mercapto-1-oxopropyl)cyclohexanecarboxylic acid is partially dissolved in a mixture of 15 ml. of 1 N sodium hydroxide and 100 ml. of water. To this rapidly stirred mixture (almost all solid in solution) is added dropwise 0.5 M of iodine in absolute ethanol. During the addition, the pH of the reaction mixture is maintained at 5.5–6.5 by dropwise addition of 1 N sodium hydroxide. The solution is stirred for fifteen minutes at room temperature, a trace of excess iodine is discharged with aqueous sodium thiosulfate, acidified with concentrated hydrochloric acid, and thoroughly extracted with ethyl acetate. The combined extracts are dried and concentrated in vacuo to give 2.1 g. (70%) of crude (trans)-2,2'-[dithiobis(1-oxo-3,1-propanediyl)]biscyclohexanecarboxylic acid. The oil is taken up in 25 ml. of ether, treated with 3 ml. of dicyclohexylamine, and allowed to stand overnight in the cold, yielding 3.3 g. (85% conversion) of bisdicyclohexylamine salt. Recrystallization from ethyl acetate/methanol gives the analytical sample (2.9 g.) m.p. 167°–170°.

The dicyclohexylamine salt is converted into (trans)-2,2'-[dithiobis(1-oxo-3,1-propanediyl)]biscyclohexanecarboxylic acid by treatment with 10% aqueous potassium bisulfate and extraction with ether.

EXAMPLE 20

(trans)-2,2'-[Dithiobis(1-oxoethyl)]biscyclohexane carboxylic acid

By substituting trans-2-(mercaptoacetyl)cyclohexanecarboxylic acid for the trans-2-(3-mercapto-1-oxopropyl)cyclohexanecarboxylic acid in the procedure of Example 19, (trans-2,2'-[dithiobis(1-oxoethyl)]biscyclohexanecarboxylic acid is obtained.

What is claimed is:

1. A compound of the formula

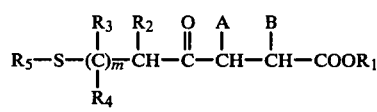

wherein $R_1$, $R_2$, $R_3$ and $R_4$ each is hydrogen or lower alkyl; $R_5$ is

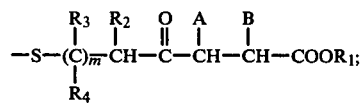

A and B each is hydrogen or join together to complete a cycloalkyl ring of 4 to 6 carbons;
each m is one;
and salts thereof.

2. A compound of the formula

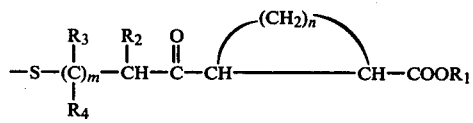

wherein $R_1$, $R_2$, $R_3$ and $R_4$ each is hydrogen or lower alkyl; $R_5$ is hydrogen, lower alkanoyl, benzoyl or

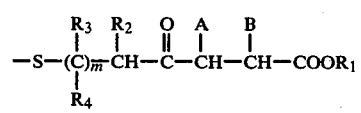

m is 0 or 1;
n is 2, 3 or 4;
and salts thereof.

3. A compound as in claim 2 wherein $R_1$, $R_2$, $R_3$ and $R_4$ each is hydrogen or lower alkyl; $R_5$ is hydrogen, lower alkanoyl or benzoyl, m is 1; n is 2, 3 or 4; and salts thereof.

4. A compound as in claim 3 wherein n is 3.

5. A compound as in claim 3 wherein n is 2.

6. A compound as in claim 3 wherein n is 4.

7. A compound as in claim 3 wherein $R_1$, $R_2$, $R_3$, $R_4$ and $R_5$ each is hydrogen.

8. A compound as in claim 3 wherein $R_1$, $R_2$, $R_3$ and $R_4$ each is hydrogen and $R_5$ is lower alkanoyl.

9. A compound as in claim 3 wherein n is 2 and and $R_1$, $R_2$, $R_3$, $R_4$ and $R_5$ each is hydrogen.

10. A compound as in claim 3 wherein n is 3 and $R_1$, $R_2$, $R_3$, $R_4$ and $R_5$ each is hydrogen.

11. A compound as in claim 3 wherein n is 4 and $R_1$, $R_2$, $R_3$, $R_4$ and $R_5$ each is hydrogen.

12. A compound as in claim 3 wherein $R_2$ is lower alkyl.

13. A compound as in claim 3 wherein $R_3$ and $R_4$ each is lower alkyl.

14. A compound as in claim 3 wherein n is 4, $R_1$, $R_3$, $R_4$ and $R_5$ each is hydrogen; and $R_2$ is methyl.

15. A compound as in claim 3 wherein n is 3; $R_1$, $R_2$ and $R_5$ each is hydrogen and $R_3$ and $R_4$ each is methyl.

16. A compound as in claim 1 wherein each $R_1$, $R_2$, $R_3$ and $R_4$ is hydrogen; each m is 1; A and B join to complete a cyclohexane ring.

17. A compound as in claim 2 wherein $R_1$, $R_2$ and $R_5$ each is hydrogen; m is 0; and n is 4.

18. A compound of the formula $$R_3 \atop R_4 \!\!\diagdown\!\! C\!=\!C \!\!-\!\! \overset{R_2}{\underset{}{C}} \!\!-\!\! \overset{O}{\underset{}{\overset{\|}{C}}} \!\!-\!\! CH \!\!-\!\! \overbrace{(CH_2)_n} \!\!-\!\! CH \!\!-\!\! COOR$$

wherein $R_2$, $R_3$, $R_4$ and n have the same meaning as in claim 2 and R is hydrogen, phenyl-lower alkyl or diphenyl-lower alkyl.

19. A compound as in claim 18 wherein R and $R_2$ each is hydrogen; $R_3$ and $R_4$ each is methyl and n is 3.

20. A compound as in claim 18 wherein R, $R_2$, $R_3$ and $R_4$ each is hydrogen and n is 4.

21. A compound as in claim 18 wherein R is diphenylmethyl; $R_2$ and $R_4$ each is hydrogen; $R_3$ is methyl; and n is 4.

22. A compound as in claim 18 wherein R is diphenylmethyl; $R_2$, $R_3$ and $R_4$ each is hydrogen; and n is 3.

23. A compound as in claim 18 wherein R, $R_2$, $R_3$ and $R_4$ each is hydrogen and n is 2.

24. A compound of the formula $$HS\!-\!(CH_2)_m\!-\!CH_2\!-\!\overset{O}{\overset{\|}{C}}\!-\!\overset{A}{\underset{}{CH}}\!-\!\overset{B}{\underset{}{CH}}\!-\!COOH$$

wherein

A and B each is hydrogen or join together to complete a cycloalkyl ring of 4 to 6 carbons;
m is 0 or 1;
and salts thereof.

25. A compound of claim 24 wherein A and B are both hydrogen and m is 1.

* * * * *

UNITED STATES PATENT AND TRADEMARK OFFICE
CERTIFICATE OF CORRECTION

PATENT NO. : 4,206,137  
DATED : June 3, 1980  
INVENTOR(S) : Michael E. Condon et al.

Page 1 of 2

It is certified that error appears in the above—identified patent and that said Letters Patent is hereby corrected as shown below:

Claim 2 should read as follows:

2. A compound of the formula

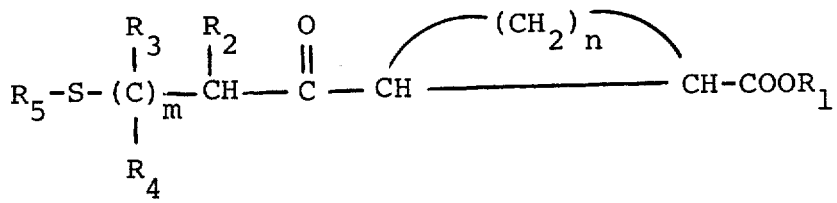

wherein $R_1$, $R_2$, $R_3$ and $R_4$ each is hydrogen or lower alkyl;

$R_5$ is hydrogen, lower alkanoyl, benzoyl or

UNITED STATES PATENT AND TRADEMARK OFFICE
CERTIFICATE OF CORRECTION

PATENT NO. : 4,206,137

DATED : June 3, 1980

INVENTOR(S) : Michael E. Condon et al.

It is certified that error appears in the above—identified patent and that said Letters Patent is hereby corrected as shown below:

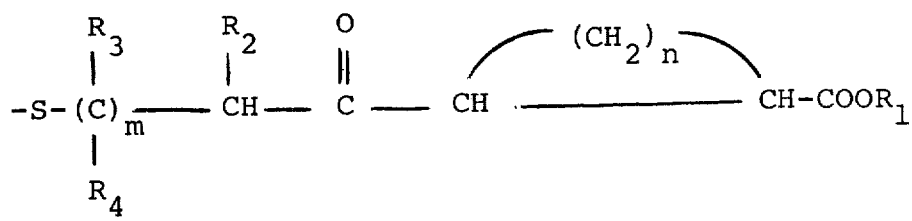

m is 0 or 1;

n is 2, 3 or 4;

and salts thereof.

Signed and Sealed this

Sixteenth Day of February 1982

[SEAL]

Attest:

GERALD J. MOSSINGHOFF

Attesting Officer

Commissioner of Patents and Trademarks